United States Patent
Carmeli et al.

(10) Patent No.: US 9,962,079 B2
(45) Date of Patent: May 8, 2018

(54) SLIT LAMP STRUCTURE FOR AN OPHTHALMOSCOPE

(71) Applicant: LUMENIS LTD., Yokneam Ilit (IL)

(72) Inventors: Tomer Carmeli, Alonei Aba (IL); Yosef Wexler, Nazareth Elith (IL); Shai Yefet, Petah Tikva (IL); Oren Liav, D.N. Misgav (IL)

(73) Assignee: LUMENIS LTD., Yokneam (IL)

( * ) Notice: Subject to any disclaimer, the term of this patent is extended or adjusted under 35 U.S.C. 154(b) by 19 days.

(21) Appl. No.: 15/169,937

(22) Filed: Jun. 1, 2016

(65) Prior Publication Data
US 2016/0353991 A1  Dec. 8, 2016

Related U.S. Application Data
(60) Provisional application No. 62/169,574, filed on Jun. 2, 2015.

(51) Int. Cl.
| | |
|---|---|
| *A61B 3/10* | (2006.01) |
| *A61B 3/135* | (2006.01) |
| *A61B 3/12* | (2006.01) |
| *A61B 3/13* | (2006.01) |
| *A61B 3/00* | (2006.01) |
| *A61B 3/14* | (2006.01) |

(52) U.S. Cl.
CPC .......... *A61B 3/135* (2013.01); *A61B 3/0075* (2013.01); *A61B 3/12* (2013.01); *A61B 3/132* (2013.01); *A61B 3/14* (2013.01)

(58) Field of Classification Search
CPC .................................................. A61B 3/135
USPC ........................................ 351/213, 214, 221
See application file for complete search history.

(56) References Cited

U.S. PATENT DOCUMENTS

| 4,257,687 A * | 3/1981 | Kohayakawa ......... A61B 3/145 351/208 |
|---|---|---|
| 7,344,248 B2 * | 3/2008 | Zorn ........................ A61B 3/12 351/205 |
| 7,347,553 B2 * | 3/2008 | Matsumoto .............. A61B 3/14 351/205 |
| 8,506,081 B2 * | 8/2013 | Matsumoto .............. A61B 3/12 351/205 |
| 2004/0002694 A1 * | 1/2004 | Pawlowski ............. A61F 9/008 606/4 |
| 2014/0139807 A1 * | 5/2014 | Uchiyama .............. A61B 3/135 351/214 |

FOREIGN PATENT DOCUMENTS

JP          06142047 A  *  5/1994

* cited by examiner

*Primary Examiner* — Thomas K Pham
*Assistant Examiner* — Nicholas R Pasko
(74) *Attorney, Agent, or Firm* — ISUS Intellectual Property PLL; A. Jason Mirabito (57) ABSTRACT

A slit lamp device for use in an ophthalmoscope includes one or more light sources for providing a light path comprised of one or more beams of: visible light and infrared (IR) light; a slit lamp control mechanism along the light path for receiving the one or more light beams and forming the one or more light beams into a slit light beam; the slit lamp control mechanism further controlling the width of the formed slit light beam; a first, narrow slit passes visible light through the slit control mechanism and a second, wider slit passes IR light though the slit control mechanism.

10 Claims, 5 Drawing Sheets

SLIT LAMP STRUCTURE FOR AN OPHTHALMOSCOPE

RELATED APPLICATIONS

The present application is related to and claims priority to U.S. Provisional Application Ser. No. 62/169,574, filed Jun. 2, 2015, the entirety of which is hereby incorporated by reference.

FIELD OF THE INVENTION

The present invention relates to improvements in the operation and structure ophthalmoscope devices.

BACKGROUND OF THE PRESENT INVENTION

The fundus of the eye is the interior surface of the eye behind the lens which includes the retina, optic disc, macula and fovea. The fundus of the eye can be directly examined through an ophthalmoscope by a physician or pictured using a fundus camera. Pupil dilation increases the field of view of the examination system and improves the quality of the image seen or obtained. The image provided may capture a significant area of the retina. Contrast agents and improved digital imaging sensors today provide high quality pan retinal images. A source of light within the ophthalmoscope or a fundus camera further improves tissue illumination and image quality. A wide set of fundus lenses are available and in common practice today in conjunction with illumination and viewing systems.

The human eye is blind to the infrared portion of the electromagnetic spectrum. However, some image sensors which are available today have at least some degree of sensitivity to the infrared spectrum. Light sources within eye fundus visualization systems may also provide some infrared output. U.S. Patent application number 2012/0239015 discloses the use of an illuminating system configured to produce visible and infrared light. Using infrared light during an eye examination has the advantage that the IR light does not create eye dazzling and therefore the patient may be able to keep his or her eyes open during the examination or treatment. This allows a continuous imaging of the eye fundus. Short pulses of visible light periodically provide a more detailed snapshot image of the fundus and may be superimposed on the continuous IR image. The above-mentioned application discloses an ophthalmoscope which is configured to deliver therapeutic laser radiation onto the fundus of the eye while acquiring and presenting real time sequences of images of the retina. Such image sequences may be compared and analyzed for the sake of monitoring a laser treatment.

The quality and magnification of an eye fundus image which is generated by an ophthalmoscope is limited. During conventional examination and treatments, a more precise and detailed picture of the target tissue may be required. A slit lamp, a common implement today, is configured to produce such images. The slit lamp is the most frequently used and most universally applicable instrument among ophthalmologists. The slit lamp is named after its illumination system which intended to produce a "slit" image which is very bright but relatively narrow. The exact distance of the slit image produced from the instrument, as well as the slit's length, width and position are fully variable and controlled by the operator. Kohler illumination optics eliminate the image of the lamp's filament from the field of view. A high luminance halogen lamp is often used to change the color of the tissue to yellow to make it more noticeable. Such color changes have diagnostic importance. A slit lamp microscope may provide a stereoscopic observation and magnification. Fundus lenses may be used in conjunction with a slit lamp to create an image of the fundus.

Typically, the slit lamp and the microscope are generally oriented perpendicular to each other, but share a common focal point and can be mutually rotated about their common focal point. Although using a slit lamp improves the image quality by magnifying the target tissue, the tradeoff is a smaller field of view. Therefore, it would be desirable to provide an instrument and method to better balance between the field of view seen and the quality of the viewed image.

SUMMARY OF THE PRESENT INVENTION

In an aspect, a slit lamp device for use in an ophthalmoscope includes one or more light sources for providing a light path comprised of one or more beams of: visible light and infrared (IR) light; a slit lamp control mechanism along the light path for receiving the one or more light beams and forming the one or more light beams into a slit light beam; the slit lamp control mechanism further controlling the width of the formed slit light beam; a first, narrow slit passes visible light through the slit control mechanism and a second, wider slit passes IR light though the slit control mechanism.

In another aspect, the second, wider slit to pass an IR light beam is enabled by one or more long-pass filters mounted in the slit lamp control mechanism in the light path.

In another aspect, the beams of visible light and IR light are provided by one of: one light source with both IR and visible light components or separate light sources.

In yet another aspect, the first, narrow slit and the second, wider slit overlap in their position in the slit control mechanism.

DETAILED DESCRIPTION OF THE PRESENT INVENTION

Figure 1:
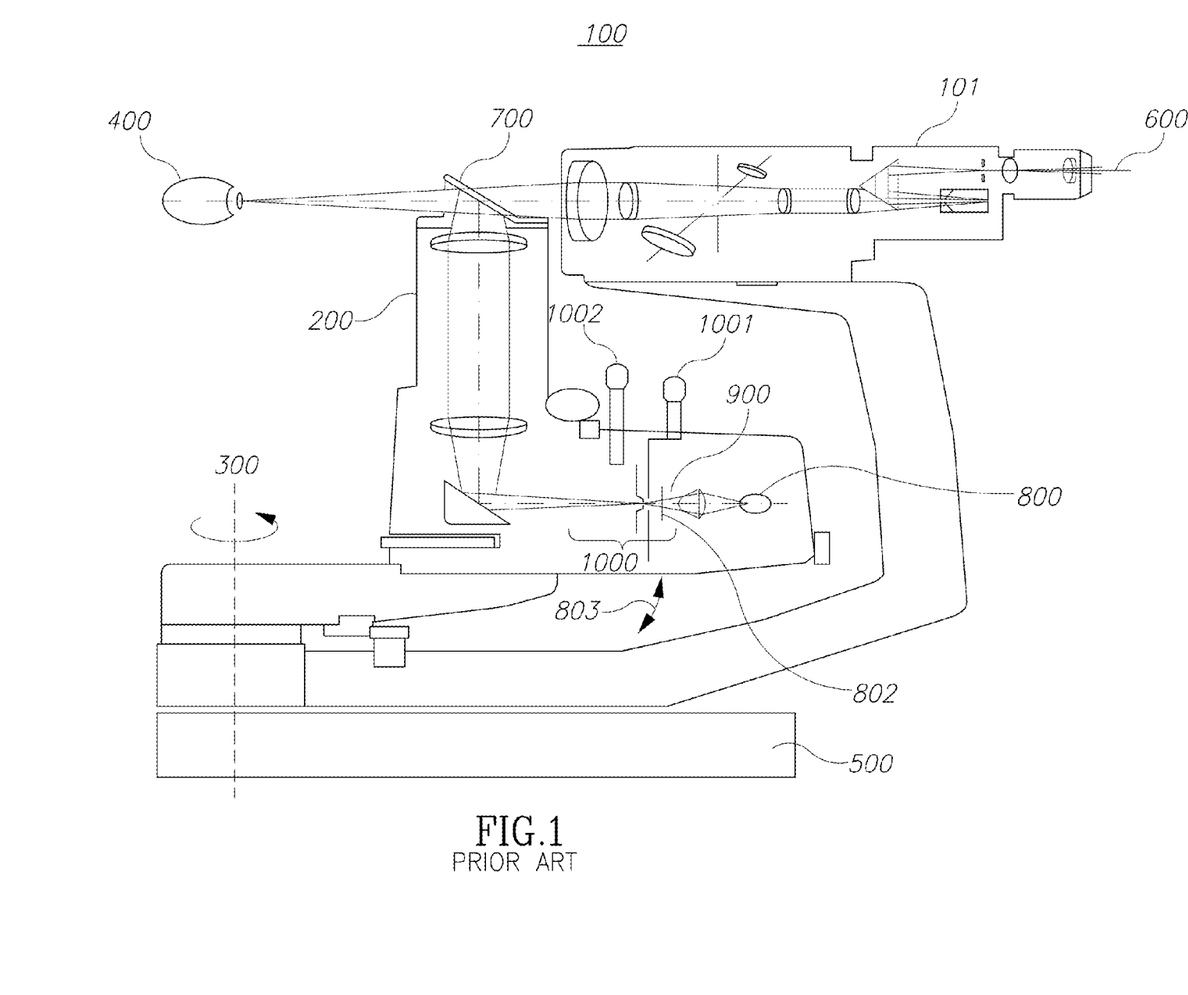
FIG. 1 illustrates the general structure of a known slit lamp device including a slit control mechanism of the present invention.

According to one aspect of the invention, there is provided a slit lamp 100 as shown in FIG. 1 having a microscope module 101 and illuminating module 200 which are configured to swing about a common vertical axis 300 independent of each other. Vertical axis 300 is located below a patient's eye 400. Mechanical support 500 is a mechanical base containing a horizontal cross slide system which is conventionally configured to be managed by a joystick control (not shown). A vertical control mechanism, typically integrated into the joystick and operated by rotation, is configured to move the slit and the viewing axis 600 vertically. Prism 700 is a narrow prism which may allow stereoscopic view during direct forward illumination without interfering with the field of view. Light source 800 produces light beam 900. Light beam 900 enters the slit control mechanism 1000 which forms the beam into a slit. Slit control mechanism 1000 is configured, as known to those skilled in the art, to manipulate slit width, length and orientation by manual manipulation of the physician through knobs 1001 and 1002.

Figure 2:
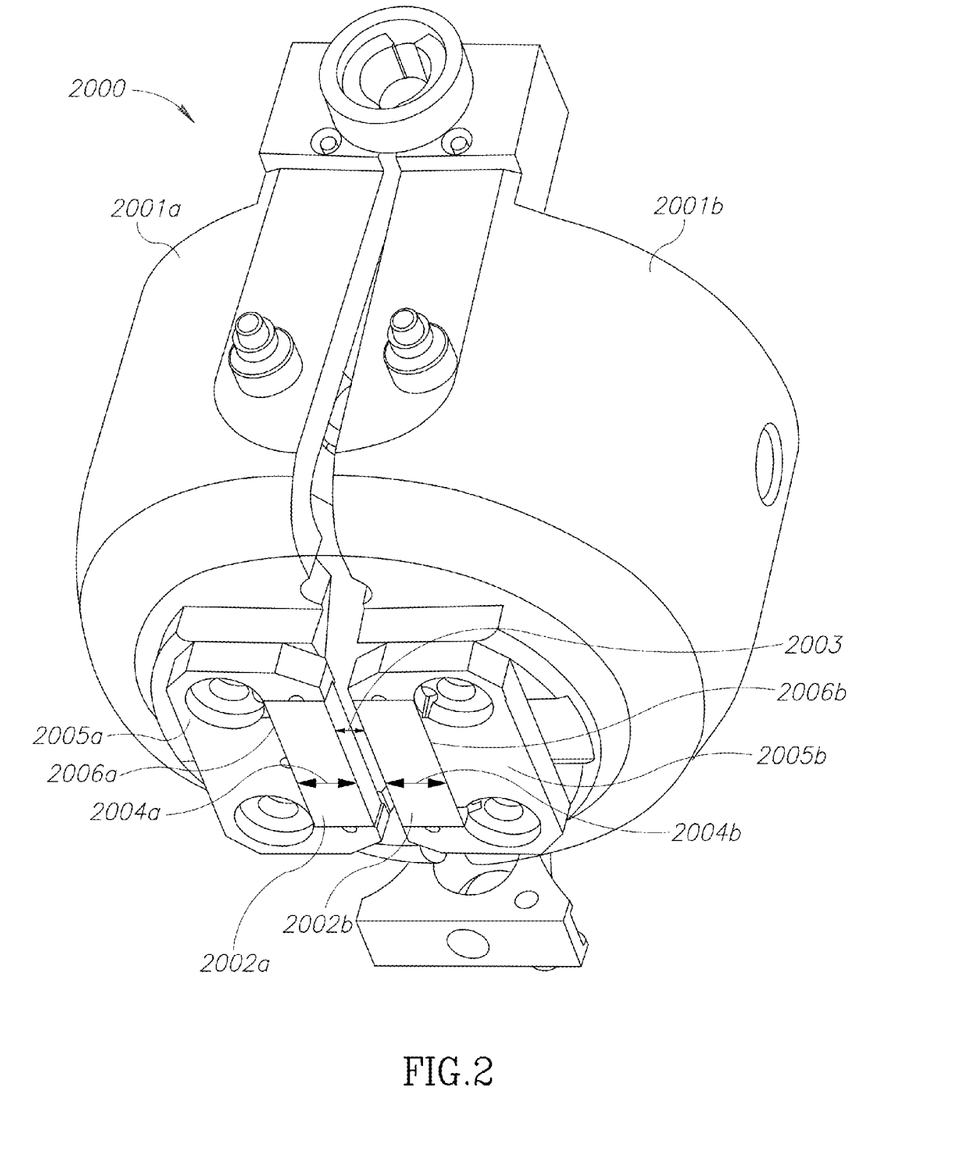
FIG. 2 illustrates a slit control mechanism in accordance with the present invention.

FIG. 2, for simplicity purposes, illustrates only part of a slit control mechanism 2000 which may be substituted for the slit control mechanism 1000 in FIG. 1. This portion of the slit control mechanism 2000 is configured to control the slit width 2003. A second mechanism includes an aperture which may be positioned distally or proximally of element 2000 and is further configured to control the slit dimensions such as height or width by changing its aperture diameter. Light source 800 is located (not shown) behind slit control mechanism 2000. Light source 800 generates both visible and IR light. Slit control mechanism 2000 consists of a first flange 2001a and second flange 2001b. Slit control mechanism 2000 may be configured to control the width 2003 between flanges 2001a and 2001b. Light generated by lamp 800 passes through slit 2003 creates a slit illumination beam which is delivered by a set of optics into the patient's eye 400 as seen, for example, in FIG. 1. The two slit control mechanisms work in tandem to control both the width and height of the illuminating slit. The orientation of the entire structure of the two orthogonal slit control mechanisms is also adjustable manually to further control the orientation of the illuminating slit.

The sharp edges of the cheeks 2002a and 2002b turn the light beam which originates from lamp 800 into a sharp edged illuminating slit beam. Slit lamps in the prior art are configured to pass light through open slit 2003 and to block all light which does not go through open slit 2003. Therefore, the field of view illuminated and examined under the prior art slit lamps is bounded by the width of the slit 2003. As mentioned above, a sharp magnified image requires a narrow slit and therefore a narrow field of view. Only a small area of the target tissue of the eye can be seen with the quality and resolution which is required for accurate examination and/or eye treatments, such as a laser treatment of the retina. In other, more advanced slit lamps which incorporate camera sensors, the same problem occurs in which only a small segment of the target tissue is exposed to the imaging sensor.

Acquiring narrow slit images of the retina may create image orientation and image registration challenges. Typically, an image may be required to be accurately registered based on real landmarks on the tissue for planning or monitoring the patient and any treatment. The retina, cornea or the sclera are examples of ophthalmic organs of interest having only a small amount of tissue landmarks and this makes it difficult to register narrow images of such organs.

Figure 3:
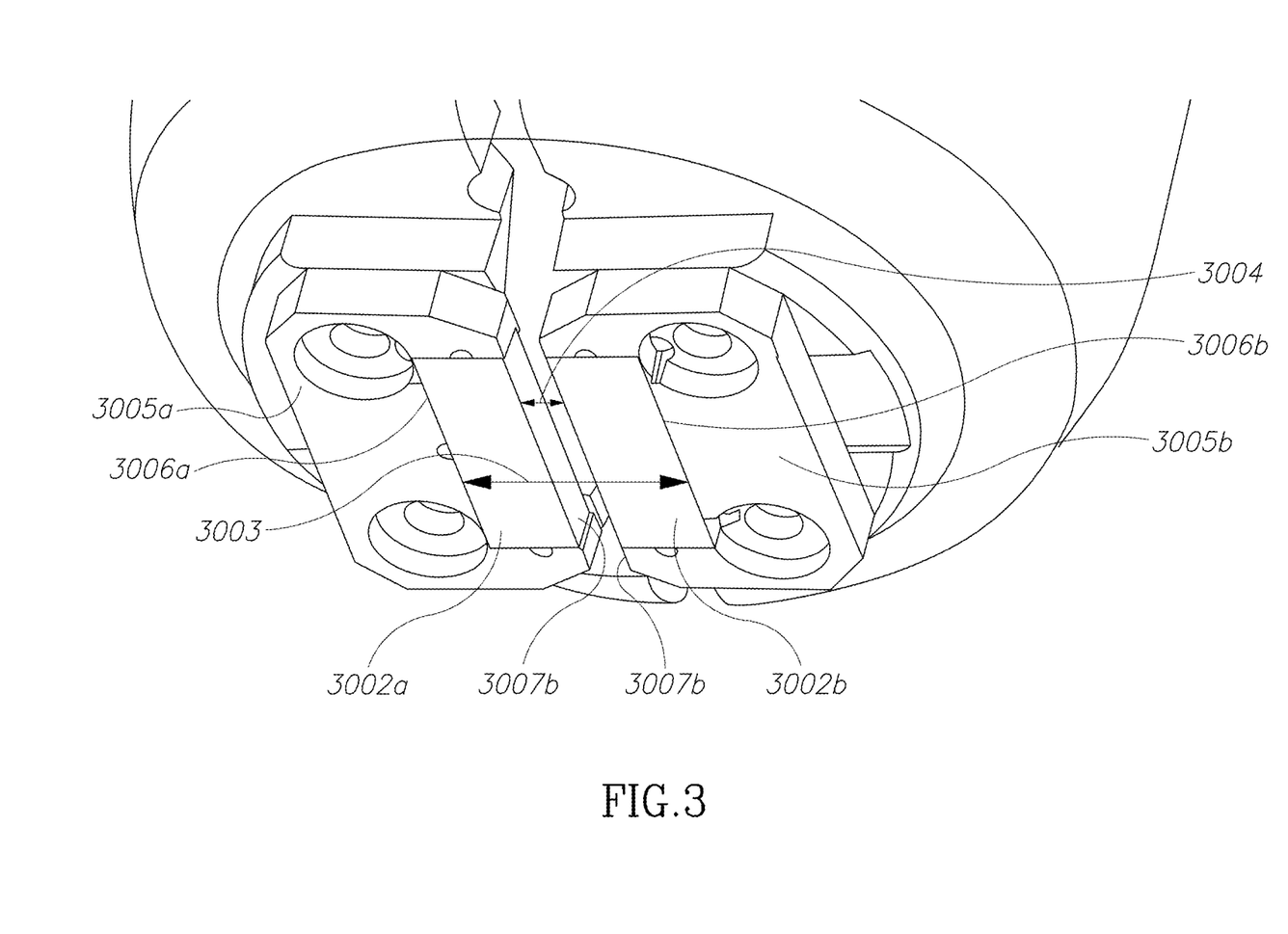
FIG. 3 illustrates another view of the slit control mechanism of the present invention.

Therefore, according to one aspect of the present invention, there is provided a slit lamp having effectively two slits. A first, narrow slit, such as slit 2003 in FIG. 2, is configured to pass visible light for providing a high quality and detailed first image. A second, wider slit, such as slit 3003 in FIG. 3, is configured to pass IR light for providing a second image. According to this aspect of the invention, illuminating module 200 is configured to deliver light originated by lamp 800 to slit control mechanisms 1000 and 2000. The light delivered is either IR light or light that is mainly visible.

Figure 5:
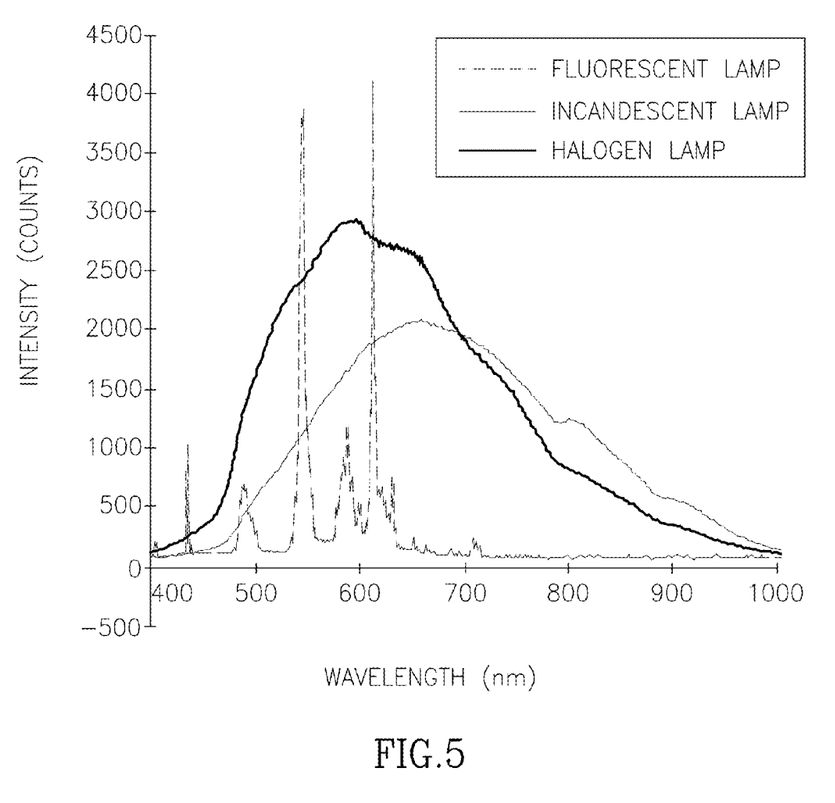
FIG. 5 illustrates a typical spectral distribution of a halogen lamp in use with slit lamps.

FIG. 5 shows a typical spectral distribution of a Halogen lamp which is in common use with slit lamps. It should be mentioned that different lamps with different spectral distributions may also be used according to the present invention and FIG. 5 is presented herein only as one non-limiting example. A long pass IR filter 802 (FIG. 1) may be positioned between lamp 800 and slit control mechanisms 1000 and 2000. Such filter may be drawn in and out of the main optical path of illuminating module 200 as shown by arrows 803 to switch between these two modes of illuminations.

According to another embodiment of the present invention, at least two lamps may be used. One lamp may be configured to deliver mainly visible light to the main optical axis of the illuminating module 200 and another lamp may be configured to deliver mainly IR light, also along the main optical axis either directly or through known mirrors or prisms. A control system may be provided to control the activation of each lamp based on user inputs.

According to another aspect of the invention, the slit lamp may further include an image sensor which is configured to acquire an IR wide image through IR slit 3003 when the target tissue is illuminated by IR radiation or a visible narrow image through visible slit 2003 when the target tissue is illuminated by mainly visible light. It should be mentioned that slits 2003 and 3003 have an overlap which is basically the width of the slit visible 2003. Also, IR and visible illuminations may be performed one after the other by one or more dedicated light sources. However, according to another aspect of the invention, lamp 800 may be configured to generate both visible and some IR radiation. An image sensor which has a least some degree of sensitivity to IR radiation may provide simultaneously wide and narrow images. Such a wide image may include a central slit area and two parallel side slits on both sides of the central slit. The central slit image may be based mainly on visible light and have a first quality. The two parallel side slits may be based on mainly IR information acquired from tissue areas on both sides of the image which are exposed to mainly IR light and therefore has a second quality. According to this aspect of invention, the first quality of the visible light based image may be better than the second quality of IR light based image.

According to another aspect of the present invention, there is provided a wide IR light based image which covers bigger areas of a target tissue and a narrower visible light based image which covers a smaller area of the target tissue than is covered by the IR based image.

Turning now to FIG. 2, cheeks 2002a and 2002b are long pass optical filters which are configured to pass mainly the illuminating IR spectrum of the lamp 800 and reflected IR light from the retina. Cheeks/high pass optical filters 2002a and 2002b have widths 2004a and 2004b respectively. High pass filters 2002a and 2002b are positioned in two outlets defined within front portions 2005a and 2005b. Front portion 2005a has an edge 2006a and front portion 2005b has an edge 2006b.

Turning now to FIG. 3, width 3003 is defined by and between edges 3006a and 3006b. Cheeks 3002a and 3002b are opaque to visible light and transparent to IR light while front portions 3005a and 3005b are opaque to both visible and IR light. Width 3003 defines a wide IR slit and long pass filters 3002a and 3002b, through their opposite close edges 3007a and 3007b, define a narrow slit 3004. According to this aspect of the invention the first slit 3003 is wider than the second slit 3004. The wider first slit is configured to form a wider IR illuminating beam originated by lamp 800 to illuminate a bigger area of the target tissue with IR light, such as the retina for example. Also, the wider first slit is configured to pass a wider IR reflected beam originated from the target tissue to an image sensor. Visible light and IR light passes the narrow slit while mainly IR light passes the wider slit, at least in the areas blocked by the long pass filters. An image sensor (not shown) is configured to capture an image of the illuminated tissue. A bigger area of the target tissue is illuminated by IR and therefore the image sensor can generate an image, at least based mainly on IR information, of a bigger tissue area than the tissue area illuminated and seen under visible light through the narrow slit.

According to another aspect of the invention, a method of illuminating and imaging a target eye tissue such as a fundus tissue is provided. The method comprises positioning a first wide IR slit and a second narrow visible slit in front of an eye tissue. The method may further comprise positioning the narrow visible slit in such a way that it is at least partially overlaps with the wider IR slit. According to one embodiment of the present invention, positioning the narrow slit is positioning the narrow slit in the center of the wide slit. The method may further comprise acquiring an image of the fundus of the eye wherein at least a portion of the image is based on information which is captured from the wide slit. Alternatively, acquiring an image of the fundus of the eye wherein the image is based on information which is captured from the wide slit and from the narrow slit.

According to another aspect of the invention, the method further includes the step of acquiring an IR image and acquiring a visible image of the fundus simultaneously or in a sequenced fashion. The acquired IR image may be wider than the acquired visible image. Furthermore, the acquired visible image may partially cover an area of the acquired IR image. According to another aspect of the invention, acquiring a visible image is accomplished by acquiring a visible image which is located in a central area of an IR image of the fundus.

According to another aspect of the invention, there is provided a method of illuminating the fundus of the eye through a slit lamp by at least two different spectral distributions. A first spectral distribution may be configured to illuminate a first portion of the eye fundus with mainly visible light and a second spectral distribution may be configured to illuminate a second portion of the eye fundus with mainly infrared (IR) light. The illuminating method may be accomplished by using different and dedicated light sources or filtering a single light source.

According to another aspect of the invention, there is provided a method of capturing an image of the fundus of the eye through a slit lamp using at least two different spectral distributions of reflected illuminating light from a target tissue. The at least two spectral distributions of the reflected light may originate from different tissue areas. Such different tissue areas may at least partially overlap. The method may further comprise acquiring an image from a first wide area and a second narrow area wherein the second narrow area is located approximately in the center of the first area. Acquiring an image from the first wide area may include acquiring an image which is mainly based on IR reflected light and acquiring an image from the second narrow area may include acquiring an image which is mainly based on reflected light which is visible light.

Figure 4:
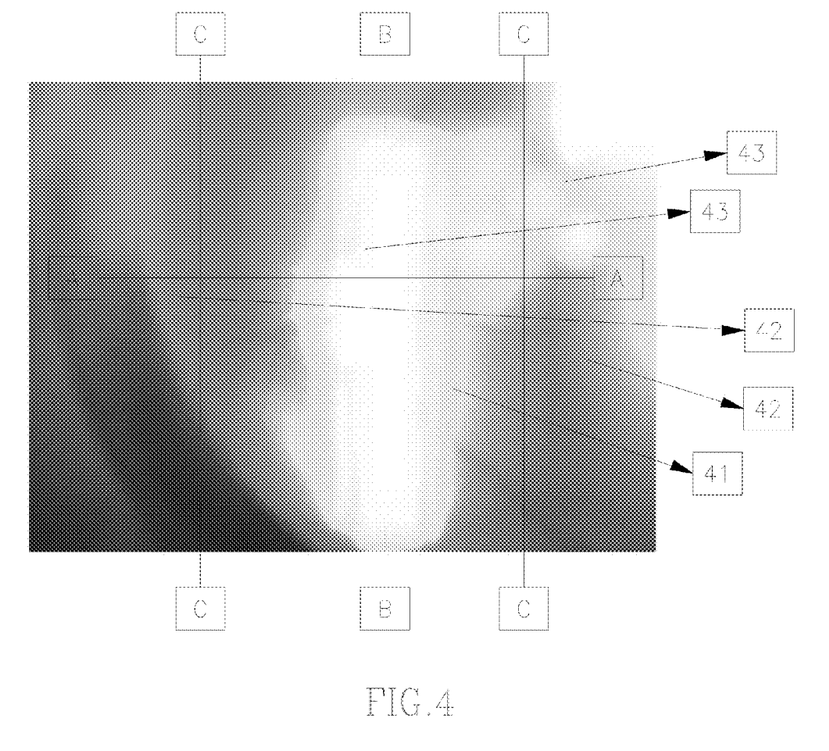
FIG. 4 illustrates an exemplary image of the eye in accordance with the present invention.

FIG. 4 shows an image acquired by a prototype developed in accordance with the present invention. A retina area 41 is located in front of a visible slit as defined above and is illuminated mainly by visible light. Areas 42 are located in front of an IR slit as defined above and are illuminated mainly by the IR spectrum of the lamp. As can be seen, the image sensor is saturated by the visible light. Areas 43 indicate intense saturation areas adjacent to the visible slit. IR slit areas 42 may also be overexposed. Optical intensity distribution across axis A-A which is approximately orthogonal to the main longitudinal axis of slits B-B and C-C of the visible slit and IR slit respectively is not homogeneous.

It is another aspect of the present invention to avoid image sensor saturation and to create an image which is more homogenous in terms of optical energy distribution along axis A-A. According to this aspect of the invention, a long pass IR filter may be positioned in front of the image sensor. The IR filter may be positioned in a fixed location or may be configured to move in and out of the optical path and the field of view of the image sensor. The system may be configured to project an image of the visible slit or the IR slit onto the image sensor through such an IR filter or without an IR filter in the path. As mentioned above, according to one embodiment of the invention, a dedicated IR lamp may be used to illuminate the retina. Alternatively, illuminating light may pass through an IR filter before it reaches the retina so that the retina is effectively illuminated mainly by IR radiation. In such cases, whether operating a dedicated IR lamp or illuminating the retina by IR radiation using a long pass IR filter, image saturation is less of an issue and the optical energy distribution along axis A-A may be homogenous enough to avoid sensor saturation and to produce a high quality image. However, when the target tissue under the visible slit is illuminated by light which mainly contains visible light, using a long pass IR filter in the field of view of the image sensor may avoid sensor saturation and improve the quality of the overall picture achieved. It should be mentioned that according to this aspect of the invention, different filters allowing the passage of different portions of the spectrum of the illuminating light may be used to achieve different balances between the optical energy distribution passes from the tissue through the visible slit to the image sensor and the optical energy distribution passes from the tissue though the IR slit to the image sensor. For example, a long pass filter which may be used to filter the light which reaches the image sensor may pass only wavelengths above 750 nm. According to another non-limiting example, such a filter may be configured to pass wavelengths above 700 nm or 650 nm or 600 nm or 550 nm or another wavelength. Controlling the spectrum and intensity of the visible optical energy passing through the visible slit and hit the image sensor may allow capturing images with different qualities providing better contrast to different pathologies based on different preferences of the physician.

The IR filter which may be located in the field of view of the image sensor, whether fixed or movable, may also have, according to another aspect of the present invention, a non-homogenous filtering capabilities across an axis A-A. A non-uniform filter may be used to avoid sensor saturation in areas adjacent to the visible slit such as areas 43 in FIG. 4. Assuming, for example, a typical visible slit of an about 0.5 mm to 1 mm while examining and treating the retina, the IR filter located in the field of view of the image sensor may be configured to pass a first spectrum in a central slit of about 1 mm which corresponds to the visible slit and to gradually pass a second spectrum in areas which correspond to the IR slit on both sides of the central visible slit. For example, the first spectrum may be a long pass spectrum above 650 nm and the second spectrum may be a long pass spectrum above 700 nm. As another example, the first spectrum may be a long pass spectrum above 600 nm and the second spectrum may be a long pass spectrum above 750 nm. Different combinations of non-homogenous spectrums may be used according to this aspect of the invention to provide better image quality and contrast for different pathologies based on different preferences by the operator.

What we claim is:

1. A slit lamp device for use in an ophthalmoscope comprising:
    a light source for providing a light beam along a light path, the light source providing a visible light beam portion and an infrared (IR) light beam portion;
    a slit lamp device along the light path including two flanges;
    a front portion mounted on each of the two flanges;
    the front portions further being coplanar and separated by a distance to define a slit therebetween in the light path;
    each front portion including a long pass optical filter mounted on each front portion, each front portion and its long pass optical filter being coplanar;
    each front portion being opaque to visible light and IR light;
    each front portion having an opening to allow light to pass through the front portion and defining an edge of the slit; and each long pass filter is mounted in the opening of each front portion extending from the edge of the slit across at least a distance of each front portion;
    wherein each long pass optical filter is opaque to visible light and transparent to IR light;
    whereby, a visible light beam portion along the light path is constrained to pass through the width of said slit only and an IR light beam portion along the light path passes through said slit and through the width of said long pass optical filter.

2. A slit lamp structure comprising:
    the slit lamp structure including two flanges;
    a front portion mounted on each of the two flanges;
    the front portions further being coplanar and separated by a distance to define a slit therebetween;
    each front portion including a long pass optical filter mounted on each front portion, each front portion and its long pass optical filter being coplanar;
    each front portion being opaque to visible light and IR light;
    each front portion having an opening to allow light to pass through the front portion and defining an edge of the slit; and each long pass filter is mounted in the opening of each front portion extending from the edge of the slit across at least a distance of each front portion; wherein each long pass optical filter is opaque to visible light and transparent to IR light;
    whereby, a light beam containing visible light along the light path is constrained to pass through the width of said slit only and a light beam containing IR light along the light path passes through said slit and through the width of said long pass optical filter.

3. A slit lamp device for use in an ophthalmoscope comprising:
    at least two light sources for providing light along a light path comprised of at least two light beams, one beam being of visible light and another beam being of infrared (IR) light;
    a slit lamp device along the light path for receiving the at least two light beams;
    the slit lamp device including two flanges;
    a front portion mounted on each of the two flanges;
    each front portion having an opening to allow light to pass through the front portion extending from an edge to define an IR slit therebetween in the light path across at least a distance of the front portion;
    a long pass optical filter mounted in each opening, each front portion being opaque to visible light and IR light;
    wherein each long pass optical filter is opaque to visible light and transparent to IR light;
    whereby, a light beam of visible light along the light path is constrained to pass through the visible light slit only and a light beam of IR light along the light path passes through said visible light slit and through said IR light slit.

4. A slit lamp device for use in an ophthalmoscope comprising:
    a light source for providing a light beam along a light path, the light source providing a visible light beam portion and an infrared (IR) light beam portion;
    a slit lamp device along the light path including two flanges;
    a front portion mounted on each of the two flanges;
    each front portion having an opening to allow light to pass through the front portion extending from an edge to define an IR slit therebetween in the light path across at least a distance of the front portion;
    a long pass optical filter mounted in each opening;
    each front portion being opaque to visible light and IR light;
    each long pass optical filter being mounted in the opening of the front portion to define a visible light slit therebetween;
    wherein each long pass optical filter is opaque to visible light and transparent to IR light;
    whereby, a visible light beam portion along the light path is constrained to pass through said visible light slit only and an IR light beam portion along the light path passes through said IR light slit and through said visible light slit.

5. A slit lamp device for use in an ophthalmoscope comprising:
    at least two light sources for providing light along a light path comprised of at least two light beams, one beam being of visible light and another beam being of infrared (IR) light;
    a slit lamp device along the light path for receiving the at least two light beams;
    the slit lamp device including two flanges;
    a front portion mounted on each of the two flanges;
    the front portions further being coplanar and separated by a distance to define a slit therebetween in the light path of the at least two light beams;
    each front portion including a long pass optical filter mounted on each front portion, each front portion and its long pass optical filter being coplanar;
    each front portion being opaque to visible light and IR light;
    each front portion having an opening to allow light to pass through the front portion and defining an edge of the slit; and each long pass filter is mounted in the opening of each front portion extending from the edge of the slit across at least a distance of each front portion;
    wherein each long pass optical filter is opaque to visible light and transparent to IR light;
    whereby, a light beam of visible light along the light path is constrained to pass through the width of said slit only and a light beam of IR light along the light path passes through said slit and through the width of said long pass optical filter.

6. The slit lamp device of claim 5, wherein the width of said slit is adjustable.

7. The slit lamp device of claim 5, further comprising a control system to control the activation of the visible light source and the IR light source.

8. The slit lamp device of claim 5, further comprising an image sensor to capture images from one or more of the visible light source and the IR light source.

9. The slit lamp device of claim 5, wherein the long pass optical filter passes wavelengths above 750 nm.

10. The slit lamp device of claim 5, wherein the long pass optical filter passes wavelengths of light above 550 nm.

* * * * *